(12) United States Patent
Walter et al.

(10) Patent No.: US 6,861,560 B2
(45) Date of Patent: Mar. 1, 2005

(54) BIS-O-AMINOPHENOLS AND PROCESSES FOR PRODUCING BIS-O-AMINOPHENOLS

(75) Inventors: Andreas Walter, Egloffstein (DE); Ingo Gnüchtel, Merching (DE); Anna Maltenberger, Leutenbach (DE); Recai Sezi, Röttenbach (DE); Horst Hartmann, Merseburg (DE)

(73) Assignee: Infineon Technologies AG, Munich (DE)

( * ) Notice: Subject to any disclaimer, the term of this patent is extended or adjusted under 35 U.S.C. 154(b) by 37 days.

(21) Appl. No.: 10/609,456

(22) Filed: Jun. 27, 2003

(65) Prior Publication Data

US 2004/0049081 A1 Mar. 11, 2004

(30) Foreign Application Priority Data

Jun. 27, 2002 (DE) ......................... 102 28 763

(51) Int. Cl.⁷ ..................... C07C 211/54; C07C 211/55
(52) U.S. Cl. ................ 564/330; 564/308; 564/335
(58) Field of Search ................. 564/330, 308

(56) References Cited

U.S. PATENT DOCUMENTS

| | | |
|---|---|---|
| 3,306,876 A | 2/1967 | Kantor et al. |
| 3,852,239 A | 12/1974 | Bellmann et al. |
| 5,696,218 A | 12/1997 | Sezi et al. |
| 6,150,558 A | 11/2000 | Sezi et al. |
| 6,518,390 B2 | 2/2003 | Okanuma et al. |
| 2002/0010370 A1 | 1/2002 | Haussmann et al. |
| 2002/0086968 A1 | 7/2002 | Haussmann et al. |
| 2003/0060573 A1 | 3/2003 | Walter et al. |

FOREIGN PATENT DOCUMENTS

| | | |
|---|---|---|
| DE | 1595724 | 4/1970 |
| DE | 2330452 | 1/1974 |
| DE | 10011604 A1 | 10/2001 |
| DE | 101 36 382 A1 | 2/2003 |
| EP | 0761717 A2 | 3/1997 |
| EP | 0 906 903 A2 | 4/1999 |
| EP | 1 132 374 A2 | 9/2001 |
| GB | 1379357 | 1/1975 |
| WO | 02/24785 A1 | 3/2002 |

OTHER PUBLICATIONS

Database CAPLUS on STN, Acc. No. 1970:74128, Korshak et al., SU 250155 (Aug. 12, 1969) (abstract).*
Chemical Abstract No. 72:74128; SU 250155 (Aug. 12, 1969) (abs).
Chemical Abstract No. 136:279843; JP 2002105034 (Apr. 10, 2002) (abs).
Chemical Abstract No. 137:48180; JP 2002/73532 (Jun. 21, 2002) (abs).

* cited by examiner

*Primary Examiner*—Brian Davis
(74) *Attorney, Agent, or Firm*—Laurence A. Greenberg; Werner H. Stemer; Ralph E. Locher

(57) ABSTRACT

A bis-o-aminophenol has a formula I

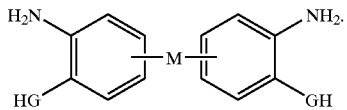

Formula I

These bis-o-aminophenols permit the preparation of polybenzoxazoles stabilized at high temperatures. The bis-o-aminophenols are preferably prepared from the corresponding diols, which are first nitrosated. The nitroso compound is then reduced to the amino compound by hydrogenation with Pd/C and $H_2$.

11 Claims, No Drawings

BIS-O-AMINOPHENOLS AND PROCESSES FOR PRODUCING BIS-O-AMINOPHENOLS

BACKGROUND OF THE INVENTION

Field of the Invention

The invention relates to bis-o-aminophenols and processes for their preparation. The bis-o-aminophenols are suitable for the preparation of poly-o-hydroxyamides which, after conversion into the corresponding polybenzoxazoles, can be used as a dielectric in microchips.

In order to avoid an inductive disturbance of signals that is caused by capacitive coupling, conductor tracks adjacent one another in microchips are insulated from one another by a dielectric disposed between the conductor tracks. Compounds that are to be used as a dielectric must meet various requirements. Thus, the signal transit time in microchips depends both on the material of the conductor track and on the dielectric which is disposed between the conductor tracks. The lower the dielectric constant of the dielectric, the shorter, too, is the signal transit time. The silica-based dielectrics used to date have a dielectric constant of about 4. These materials are gradually being replaced by organic dielectrics that have a substantially lower dielectric constant. The dielectric constant of these materials is generally below 3.

In microchips customary at present, the conductor tracks preferably are made of aluminum, AlCu, or AlCuSi. With increasing integration density of the memory chips, there is a changeover to copper as conductor track material, owing to its lower electrical resistance in comparison with aluminum. Copper permits shorter signal transit times and hence a reduction in the conductor track cross section. In contrast to the techniques customary to date in which the dielectric is filled into the trenches between the conductor tracks, in the copper damascene technique, the dielectric is first structured. The-resulting trenches are first coated with a very thin barrier that, for example, includes titanium, titanium nitride, tantalum, tantalum nitride, silicon carbide, silicon nitride, or silicon carbonitride. This barrier is necessary to avoid metal atoms diffusing out of the conductor track into the surrounding dielectric when the production of the microchips includes production stages that require temperatures of 400° C. or higher. Thereafter, the trenches are first filled with copper and then excess copper is mechanically ground away. The dielectric must therefore be stable to the materials used for grinding and must have sufficient adhesion to the substrate in order to avoid becoming detached during the mechanical grinding process. Furthermore, the dielectric must have sufficient stability in the subsequent process steps in which further components of the microchip are produced. For this purpose, it must have, for example, sufficient thermal stability and must not undergo decomposition even at temperatures of more than 400° C. Moreover, the dielectric must be stable to process chemicals, such as solvents, strippers, bases, acids, or aggressive gases. Further requirements are good solubility and a sufficient shelf-life of the precursors from which the dielectrics are produced.

Polybenzoxazoles (PBOs) are polymers that have very high heat resistance. The substances are already used for the production of protective and insulating layers. Polybenzoxazoles can be prepared by cyclization of poly-o-hydroxyamides. The poly-o-hydroxyamides have good solubility in organic solvents and good film formation properties. They can be applied to electronic components in a simple manner by using the spin-coating technique. After a thermal treatment in which the poly-o-hydroxyamide is cyclized to give the polybenzoxazole, a polymer that has the desired properties is obtained. Polybenzoxazoles also can be processed directly in their cyclized form. In this case, however, there are as a rule difficulties with the solubility of the polymer. The mechanism taking place in the cyclization of poly-o-hydroxyamides to polybenzoxazoles is shown schematically below:

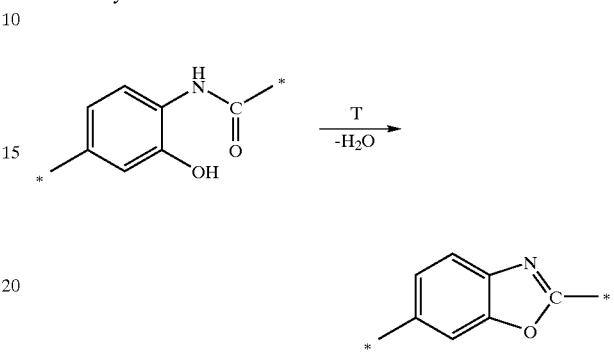

On heating, the o-hydroxyamide cyclizes to give the oxazole. Water is liberated.

The poly-o-hydroxyamides are prepared by reacting bis-o-aminophenols with dicarboxylic acids. The properties of the poly-o-aminophenol and of the polybenzoxazole prepared therefrom are substantially determined by the monomers used as starting material. Thus, not only the thermal, electrical and mechanical behavior but also the solubility, stability to hydrolysis, storability and numerous other properties of the polymers are influenced by the type of aminophenol used in the preparation. In order to be able to provide polybenzoxazoles that can be used in microelectronics as a dielectric between two metal planes, for example in multi-chip modules, memory chips and logic chips, or as a buffer layer between the chip and its housing, it is necessary to provide starting materials which impart good electrical, chemical, mechanical, and thermal properties to the polymer. Monomers for the preparation of readily soluble polybenzoxazole precursors are described, for example, in U.S. Pat. No. 4,525,539 to Feiring or European Patent No. EP 317 942. Owing to the constantly growing requirements with regard to the efficiency of the microchips and the associated miniaturization of the semiconductor components, however, a constant further development of the polymer materials is necessary in order to be able to fulfill the mechanical, electrical and chemical properties required for the polymers even with decreasing dimensions of the components. This in turn requires further development of the available monomers for the preparation of polybenzoxazoles or their soluble precursors.

SUMMARY OF THE INVENTION

It is accordingly an object of the invention to provide bis-o-aminophenols and processes for producing bis-o-aminophenols that overcome the hereinafore-mentioned disadvantages of the heretofore-known devices of this general type and that provide novel starting materials that permit the preparation of insulating polymers that have a low dielectric constant and high heat stability and stability to chemicals.

With the foregoing and other objects in view, there are provided, in accordance with the invention, bis-o-aminophenols of the formula I Formula I

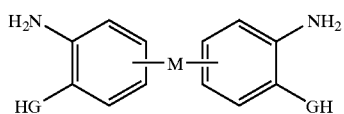

G is oxygen or sulfur.

M is

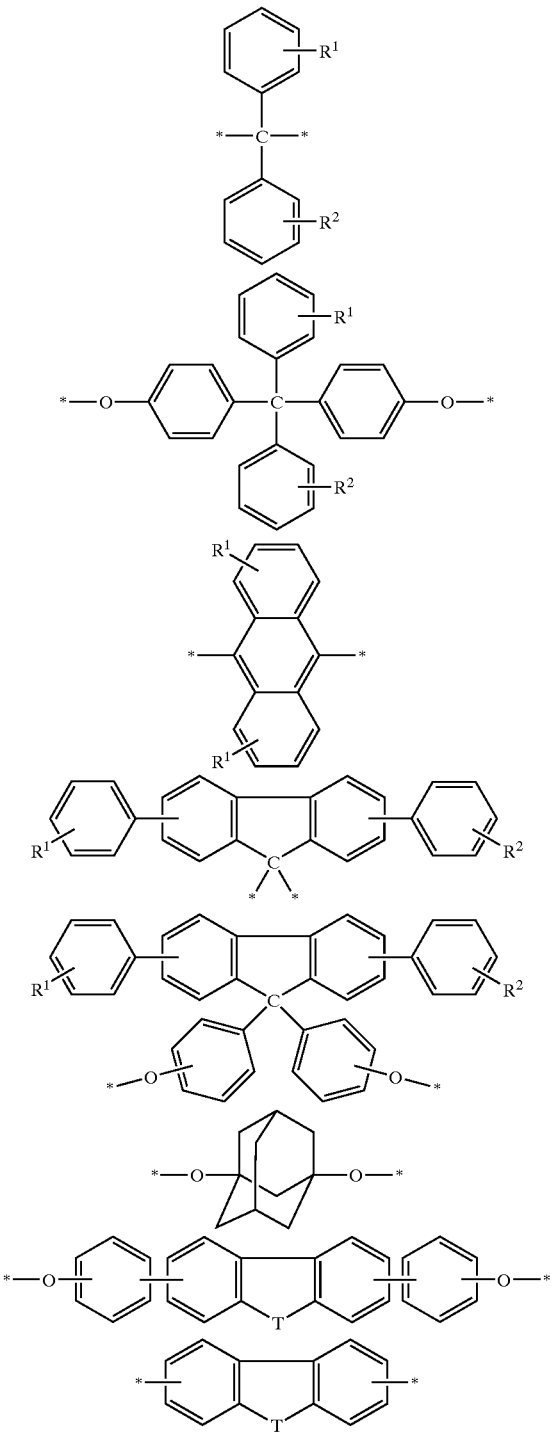

$R^1$, $R^2$, in each case independently, are

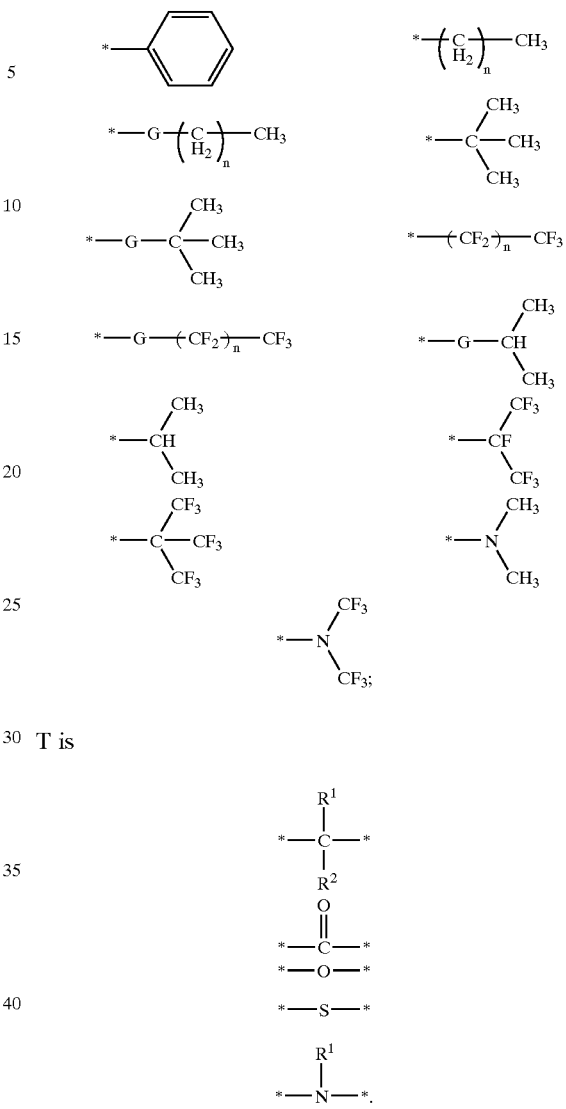

T is

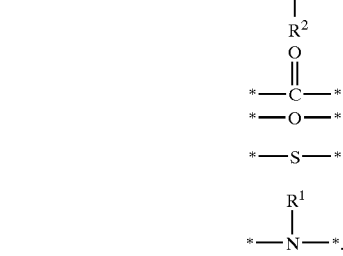

n is an integer from 0 to 5.

The bis-o-aminophenols of the formula I, according to the invention, are suitable for the preparation of poly-o-hydroxyamides, from which polymeric dielectrics which have a dielectric constant of $k \leq 2.7$ can be obtained. These polymers are very suitable for filling narrow trenches. After the cyclization of the poly-o-hydroxyamide, polybenzoxazoles which have high resistance to process chemicals, such as solvents, strippers, bases, acids or aggressive gases, are obtained. These polymers are also outstandingly suitable for the copper damascene technique. During the grinding process in which excess copper is removed, no disadvantageous effects, such as delamination, cracking, or bubble formation, occur. The adhesion of such dielectrics to the surfaces relevant for chip technology, such as silicon, silicon carbide, silicon carbonitride, silicon nitride, silica, titanium, tantalum, titanium nitride, tantalum nitride, or silicon oxynitride, is very good. The polymers prepared from the bis-o-aminophenols according to the invention are very soluble in many organic solvents. Suitable solvents are, for example, acetone, cyclohexanone, diethylene mono- and diethyl ether, N-methylpyrrolidone, γ-butyrolactone, ethyl lactate, methoxymethyl acetate, tetrahydrofuran, or ethyl acetate. They can be readily processed by spin coating, spraying or dipping techniques and give films of very good quality. The polybenzoxazoles derived from the bis-o-aminophenols according to the invention moreover have very high thermal stability.

Bis-o-aminophenols of the formula II

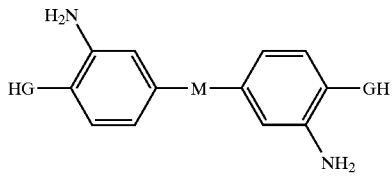

FORMULA II in which M and G have the abovementioned meaning, are particularly preferred. The bis-o-aminophenols of the formula II can be prepared in high yields and high isomer purity, which substantially simplifies the purification of the products. The bis-o-aminophenols of the formula II can therefore be made available economically.

The bis-o-aminophenols according to the invention are divided into bis-o-aminothiophenols (G=S) and bis-o-aminophenols (G=O). For the sake of simplicity, both classes of compound are combined under the term "bis-o-aminophenols". Although polymers having advantageous properties can also be prepared using bis-o-aminothiophenols, the bis-o-aminophenols (G=O) are of greater importance since, owing to their higher stability to oxidation, they can be more easily processed. Among the bis-o-aminophenols of the formula I, the compounds in which G is an oxygen atom are therefore preferred.

In order to be suitable for industrial use, it is important that the bis-o-aminophenols of the formula I be obtainable in a simple and economical manner. The invention therefore also relates to a process for the preparation of bis-o-aminophenols of the formula I, wherein a diol of the formula III

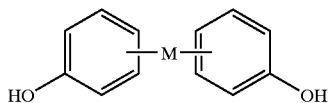

Formula III in which M has the meaning previously, is nitrosated with a nitrosating agent to give the nitroso compound, and the nitroso compound is then reduced to the bis-o-aminophenol of the formula I.

For the preparation of the bis-o-aminophenols of the formula I, the diol of the formula III is first dissolved in a suitable inert solvent at room temperature. Suitable solvents are, for example, alcohols, such as ethanol, isopropanol or butanol, acetonitrile, esters, such as ethyl acetate or propyl acetate, ketones, such as acetone, methyl ethyl ketone or diethyl ketone, or chlorinated hydrocarbons, such as chloroform, dichloromethane or methylene chloride. The solution preferably contains from 5 to 30% by weight of the diol of the formula III which is used as a starting material. Thereafter, a suitable nitrosating agent is added and the mixture obtained is stirred at temperatures of, preferably, from −15 to 40° C., in particular from 5 to 15° C., until virtually complete conversion of the starting material has taken place. Suitable reaction times are in general in the range of 1–10 hours, in particular 2–4 hours. In order to separate off the resulting nitroso compound, the solvent is first evaporated, preferably under reduced pressure. The nitroso compound can then be purified by recrystallization from a suitable solvent or by separation by column chromatography using a suitable eluent.

The advantage of the process according to the invention is firstly that the diol of the formula III, which is used as a starting material, has sufficient reactivity to achieve substantially complete conversion of the dihydroxy compound within periods of interest for industrial use. Furthermore, the hydroxyl groups of the dihydroxy compound of the formula III need not be protected by a protective group, so that operations for introduction and elimination of a protective group are dispensed with. If the hydroxyl group is in the para position relative to the group M, the nitroso group is selectively introduced into the phenyl ring in the ortho position relative to the hydroxyl group, so that, in the subsequent purification, no removal of undesired isomers is required. This too contributes to the economical preparation of the bis-ortho-aminophenols of the formula I.

All customary nitrosating agents can be used for the nitrosation. For example, isoamyl nitrite, alkyl nitrites and a mixture of sodium nitrite and concentrated sulfuric acid are suitable.

The purified bis-o-nitroso compound is then reduced to the bis-o-amino compound. For this purpose, the nitroso compound is first dissolved in a suitable solvent. For example, ethers, such as tetrahydrofuran or dioxane, are suitable. The reduction to the amino group is preferably effected with hydrogen under catalysis by a suitable catalyst. In order to accelerate the reaction, the hydrogenation is advantageously effected at elevated hydrogen pressure. A suitable catalyst is, for example, palladium on active carbon.

The bis-o-aminophenols of the formula I can also be prepared via the corresponding nitro compounds. The invention therefore also relates to a process for the preparation of bis-o-aminophenols of the formula I, wherein a diol of the formula IV

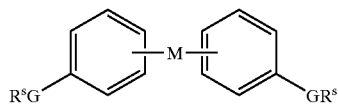

Formula IV in which M and G have the meanings stated previously and $R^s$ is a protective group, is nitrated with a nitrating agent to give the nitro compound, and the nitro compound is then reduced to the bis-o-aminophenol of the formula I.

The nitration of the protected diol of the formula IV is effected using customary nitrating reagents, for example nitric acid, nitric acid/sulfuric acid mixtures, dinitrogen pentoxide, or acetyl nitrate. In this reaction, however, it is necessary for the hydroxyl groups of the starting material to be protected by corresponding protective groups $R^s$. After a purification of the bisnitro compound, the nitro group is reduced to the amino group. For this purpose, the bisnitro compound is dissolved in a suitable solvent, for example tetrahydrofuran, a catalyst is added, for example palladium on active carbon, and hydrogenation is effected with hydrogen in an autoclave.

The protective group $R^s$ is suitably chosen so that it is reductively eliminated during the reduction of the nitro group to the amino group. In this case, the elimination of the protective group $R^s$ requires no additional production step. A benzyl group is particularly suitably used as the protective group $R^s$.

The bis-o-aminophenols of the formula I can be reacted with dicarboxylic acids or their activated derivatives to give the desired poly-o-hydroxyamides. For this purpose, the bis-o-aminophenols of the formula I are reacted with a dicarboxylic acid or an activated dicarboxylic acid derivative of the formula V

FORMULA V

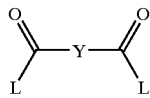

in which L is a hydroxyl group or an activating group and Y is in principle any divalent hydrocarbon radical. For example, acid chlorides or activated esters, for example sulfonic esters, can be used as an activating group for the dicarboxylic acid derivatives of the formula V. The reaction of the bis-o-aminophenols of the formula I and of the dicarboxylic acids of the formula V can, however, also be effected in the presence of a compound which activates the carboxylic acid, such as, for example, carbonyldiimidazole or dicyclohexylcarbodiimide. In principle, all reagents that bind the water formed in the reaction to themselves are suitable. For the preparation of the poly-o-hydroxyamides, the bis-o-aminophenols of the formula I and the dicarboxylic acid or optionally the dicarboxylic acid derivative of the formula V are reacted in an organic solvent at from –20 to 150° in the course of from 5 to 20 hours. If required, the terminal groups of the polymer can be blocked with a suitable reagent. The poly-o-hydroxyamide formed after the reaction is precipitated by dropwise-addition of the reaction solution to a precipitating agent, washed and dried. Suitable precipitating agents are water and alcohols, such as isopropanol, butanol or ethanol. Mixtures of these precipitating agents can also be used. The precipitating agent can also suitably contain from 0.1 to 10% of ammonia. The precipitated polymer can be directly further processed by filtration and drying and, for example, dissolved in one of the solvents mentioned further above for application to a semiconductor substrate.

The polymerization to give the poly-o-hydroxyamide can be carried out in the presence of a base in order to trap acid liberated. Suitable basic acid acceptors are, for example, pyridine, triethylamine, diazabicyclo-octane, or polyvinylpyridine. However, other basic acid acceptors also may be used. Compounds that are readily soluble in the solvent used for the synthesis, for example N-methylpyrrolidone, and in the precipitating agent, for example water or water/alcohol mixtures, or those which are completely insoluble in the solvent, such as, for example, crosslinked polyvinylpyridine, are particularly preferred. The acid acceptors can then readily be separated from the resulting poly-o-hydroxyamide during the working-up of the reaction product.

Particularly suitable solvents for the polymer synthesis are γ-butyrolactone, tetrahydrofuran, N-methylpyrrolidone and dimethylacetamide. However, in principle any solvent in which the starting components are readily soluble can be used.

The poly-o-hydroxyamides prepared in this manner can be converted into the desired polybenzoxazoles by heating with cyclization according to the mechanism explained above. Owing to their good electrical, mechanical and chemical properties, the polybenzoxazoles are very suitable for use in microelectronics.

Other features that are considered as characteristic for the invention are set forth in the appended claims.

Although the invention is illustrated and described herein as embodied in bis-o-aminophenols and processes for producing bis-o-aminophenols, it is, nevertheless, not intended to be limited to the details shown since various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying examples.

DESCRIPTION OF THE PREFERRED EMBODIMENTS

The invention is explained in more detail on the basis of examples.

EXAMPLE 1

Synthesis of 3,3'-diamino-4,4'-dihydroxytetraphenylmethane

Synthesis Route:

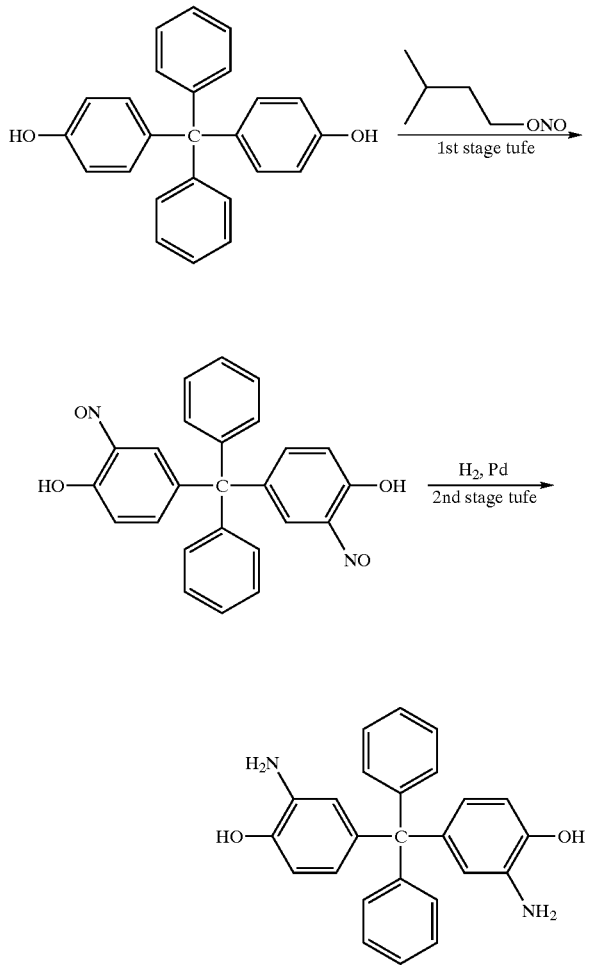

Stage 1: Nitrosation 20.07 g (0.057 mol) of 4,4'-dihydroxytetraphenylmethane are dissolved in 100 ml of glacial acetic acid, and 20 ml of isoamyl nitrite are added dropwise at RT. The course of the reaction is monitored by thin-layer chromatography until starting material is no longer detectable. 100–200 ml of water are added, and the precipitated solid is filtered off.

This is triturated with methanol and allowed to stand for several hours. After filtration with suction and drying, the product is taken up in hot toluene and subjected to fractional crystallization.

Yield: 21.27 g (91% of theory)

Stage 2: Hydrogenation and Isolation as Hydrochloride

The hydrogenation is effected according to known methods for the hydrogenation of nitro compounds, as described, for example, in European Patent Application No. EP 905 121 (which corresponds to U.S. Pat. No. 6,320,081), example 8.

20.5 g (0.05 mol) of 4,4'-dihydroxy-3,3'-dinitroso-tetraphenylmethane are dissolved in 250 ml of tetrahydrofuran (THF), and 2.00 g of 5% Pd—C are added under inert gas. The suspension is introduced under Ar inert gas into a previously heated hydrogenation reactor and is hydrogenated at room temperature for 24 h and 2 bar $H_2$ pressure. After a hydrogenation time of 24 h, the suspension is transferred under inert gas into 150 ml of analytical-grade ethanol. 10 ml of concentrated HCl are added to the mixture while stirring, and, when the product has completely dissolved, the mixture is filtered three times over a Buchner funnel to remove the Pd catalyst. The solution thus obtained is evaporated down at 70° C. and 300 mbar until about 20 ml of ethanol remain and is added with rapid stirring to a solution of 700 ml of diethyl ether and 30 ml of acetone (Selectipur). The suspension is stored for 24 h at –18° C. The solid is then filtered off with suction and dried.

Yield: 21.39 g (94% of theory)

EXAMPLE 2

Synthesis of 9,10-bis(3-amino-4-hydroxyphenyl)anthracene

Synthesis Route:

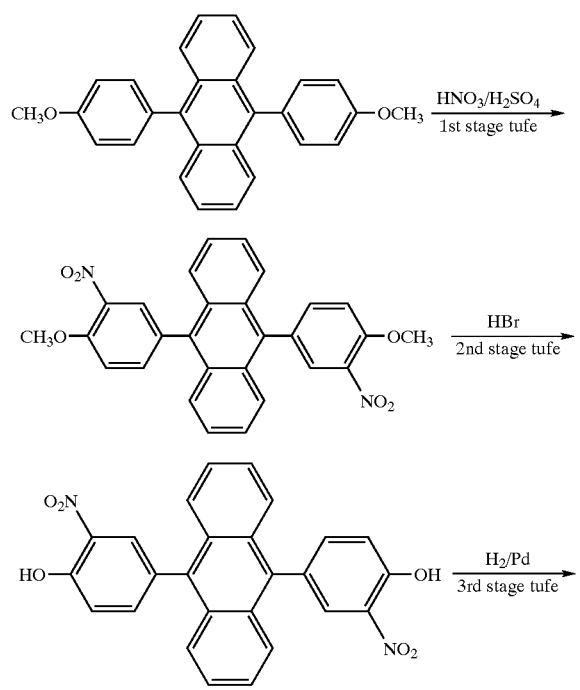

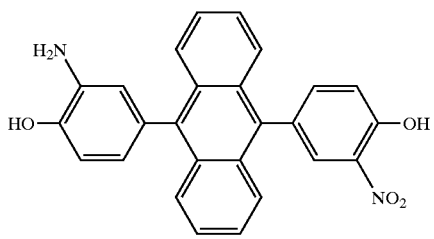

Stage 1: 9,10-Bis(4-methoxy-3-nitrophenyl)anthracene 23.43 g (60 mmol) of 9,10-bis(4-methoxy)anthracene in 250 ml of acetic anhydride are initially introduced and dissolved. A solution of 18.7 ml (0.184 mol) of nitric acid (62% strength) in 100 ml of acetic anhydride is then added dropwise in the course of 30 min to the solution at 0° C. At the same temperature, stirring is effected for 4 h and the precipitated solid is filtered off with suction on a frit. After the end of the reaction, the mixture is carefully poured into 500 ml of ice water and thoroughly stirred. The product is filtered off with suction, washed thoroughly with water and recrystallized. For this purpose, the crude product is dissolved at room temperature in toluene (2 ml/g) and heated to 90° C., and petroleum ether (4 ml/g) is added until crystallization begins. The mixture is then slowly cooled to RT. The suspension is stored for 4 h in a freezer at –18° C. and then filtered. The product is dried for 24 h at 200 mbar and 55° C.

Yield: 21.9 g (766 of theory)

Stage 2: 9,10-Bis(4-hydroxy-3-nitrophenyl)anthracene 19.2 g (0.04 mol) of 9,10-bis(4-methoxy-3-nitrophenyl)-anthracene in a mixture of 200 ml of butanone and 200 ml of concentrated HBr are refluxed for 24 h while stirring. After the end of the reaction, the suspension is evaporated down to half its volume in a rotary evaporator and the product is filtered off with suction. Recrystallization from toluene is then effected.

Yield: 16.64 g (92% of theory)

Stage 3: 9,10-Bis(3-amino-4-hydroxyphenyl)anthracene

The hydrogenation is effected according to the known methods for hydrogenating nitro compounds, as described, for example, in European Patent Application No. EP 905121, example 8.

13.56 g (30 mmol) of 9,10-bis(4-hydroxy-3-nitrophenyl)-anthracene are dissolved in 300 ml of THF, and 3.00 g of 5% Pd—C are added under inert gas. The suspension is introduced under Ar inert gas into a previously heated hydrogenation reactor and hydrogenated at room temperature for 24 h and at 2 bar $H_2$ pressure. After a hydrogenation time of 24 h, the suspension is transferred under inert gas into 100 ml of analytical-grade ethanol. 10 ml of concentrated HCl are added to the mixture while stirring and, when the product has completely dissolved, the mixture is filtered 3 times over a Buchner funnel in order to remove the Pd catalyst. The solution thus obtained is evaporated down at 70° C. and 300 mbar until about 20 ml of ethanol remain and is added to a solution of 500 ml of diethyl ether and 20 ml of acetone (Selectipur) with rapid stirring. The product is precipitated in the form of dark violet crystals. The suspension is stored for 24 h at –18° C. The solid is then filtered off with suction and dried.

Yield: 12.37 g (89% of theory)

EXAMPLE 3

Synthesis of 4,4'-di(3-amino-4-hydroxyphenoxy)tetraphenylmethane

Synthesis Route:

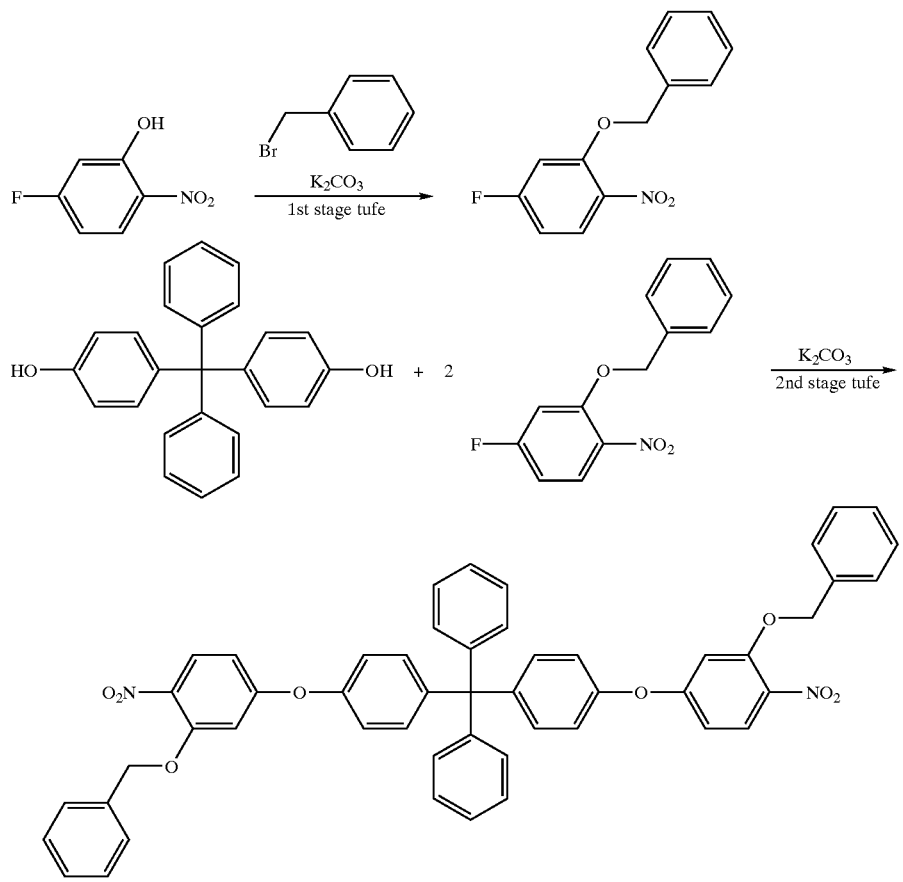

Stage 1: 3-Benzyloxy-4-nitrofluorobenzene 157 g (1.00 mol) of 3-fluoro-6-nitrophenol are initially taken in 500 ml of acetonitrile in a three-necked flask (KPG stirrer, reflux condenser, inert gas connection), and 174 g (1.02 mol) of benzyl bromide and 345 g (2.50 mol) of potassium carbonate are added in this sequence under inert gas. The mixture is refluxed for 3 hours at 90° C. After cooling to room temperature, the mixture is filtered with suction and the remaining solid is rinsed twice with 100 ml of acetonitrile each time. The solution is evaporated down until it crystallizes, and the crude product is filtered off with suction. The crude product is dissolved at room temperature in ethyl acetate (1 ml/g of crude product) and precipitated with hexane (3.6 ml/g of crude product). The mixture is stored overnight at T<−10° C. for complete crystallization.

Yield: 194 g (80% of theory),
Melting point: 58° C.

Stage 2: 4,4'-Di(4-benzyloxy-3-nitrophenoxy)-tetraphenylmethane 30.74 g (87.3 mmol) of 4,4'-dihydroxytetraphenylmethane and 43.65 g (176 mmol) of 3-fluoro-6-nitrobenzyloxyphenol are initially taken in a three-necked stirred flask equipped with an inert gas connection, KPG stirrer and reflux condenser. 350 ml of N,N-dimethyl-formamide are added to this mixture at room temperature. 61.0 g (354 mmol) of $K_2CO_3$ are added to the solution under inert gas and the solution is refluxed at 135° C. for 4 h. The progress of the reaction is checked hourly by thin-layer chromatography (eluent: petroleum ether (fraction 80–120° C.): ethyl acetate=2:1 ($R_{f,product}$=0.49)). After complete conversion, the suspension is cooled to room temperature and poured into aqueous KOH solution (350 ml of $H_2O$/7.2 g of KOH/100 g of ice). The product is precipitated in the form of yellow crystals. The precipitation is accelerated by adding about 20 ml of ethyl acetate. The product is filtered off, rinsed once with 200 ml of $H_2O$ and then poured into 350 ml of acetic acid solution (320 ml of $H_2O$/30 ml of concentrated glacial acetic acid). The solution is stirred for 30 min and the product is filtered off and additionally washed twice with 200 ml of $H_2O$.

60 g of the crude product are dissolved in 350 ml of tetrahydrofuran and heated to the boil. The solution is kept at the boiling point for 30 min and then filtered. The solution is heated again to the boil and stirred for a further 30 min. Petroleum naphtha (boiling range 60–80° C.) is added dropwise until precipitation of the product begins at 65° C. The solution is allowed to cool to room temperature and is stored for 24 h in a refrigerator at 4° C. The product is separated off by filtration and rinsed with twice 100 ml of petroleum naphtha (fraction 60–80° C.). The recrystallized product is dried at 50° C./200 mbar for 24 h.

Yield: 63.35 g (90% of theory)

Stage 3: 4,4'-Di(3-amino-4-hydroxyphenoxy)tetraphenylmethane as the Hydrochloride The hydrogenation is effected according to known methods with the hydrogenation of nitro compounds, as described, for example, in European Patent No. EP 905121, example 8.

54.48 g (67.57 mmol) of 4,4'-di(4-benzyloxy-3-nitrophenoxy)tetraphenylmethane are dissolved in 600 ml of THF, and 5.00 g of 5% Pd—C are added under inert gas. The suspension is introduced under Ar inert gas into a previously heated hydrogenation reactor and hydrogenated at room temperature for 24 h and at 2 bar $H_2$ pressure. After a hydrogenation time of 24 h, the suspension is transferred under inert gas into 200 ml of analytical-grade ethanol. 10 ml of concentrated HCl are added while stirring. After the product has completely dissolved, the mixture is filtered three times over a Buchner funnel to remove the Pd catalyst. The solution thus obtained is evaporated down at 70° C. and 300 mbar until about 30 ml of ethanol remain and is added to a solution of 700 ml of diethyl ether and 30 ml of acetone (Selectipur) with rapid stirring. The product is precipitated in the form of dark violet crystals. The suspension is stored for 24 h at −18° C. and the solid is then filtered off with suction and dried.

Yield: 37.46 g (87% of theory).

We claim:

1. A bis-o-aminophenol having a formula I

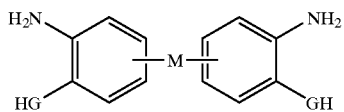

Formula I wherein

G is a heteroatom selected from the group consisting of oxygen and sulfur;

M is a substituent selected from the group consisting of:

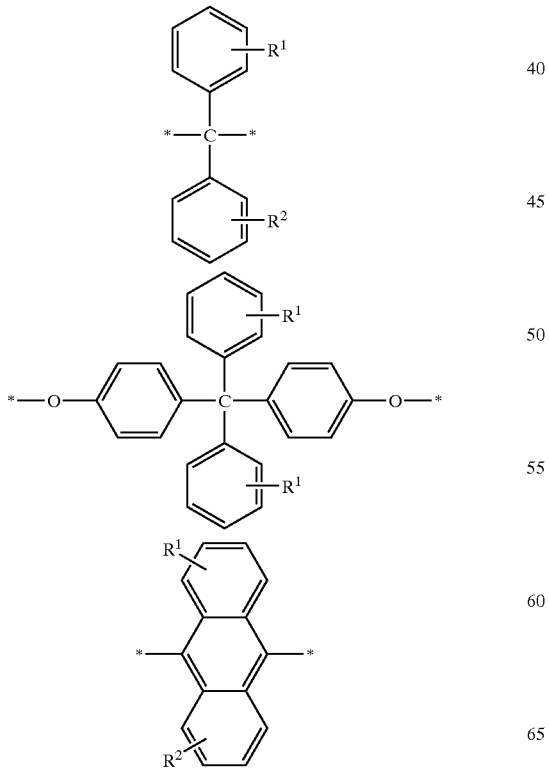

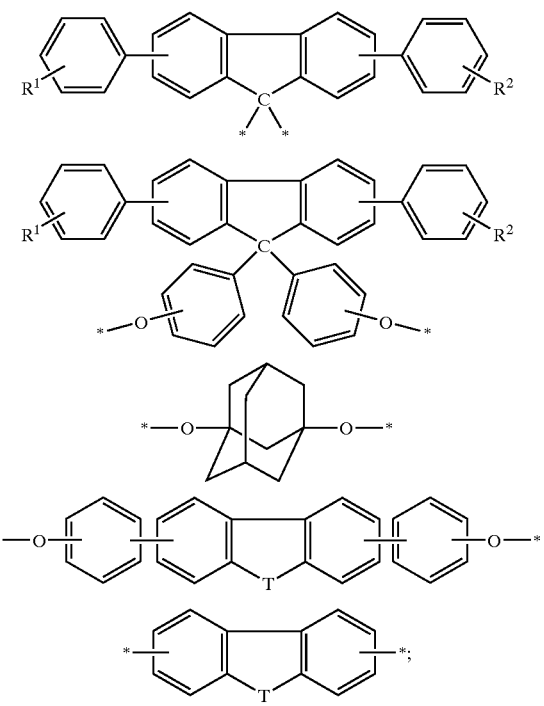

$R^1$, $R^2$, in each case independently, are substituents selected from the group consisting of:

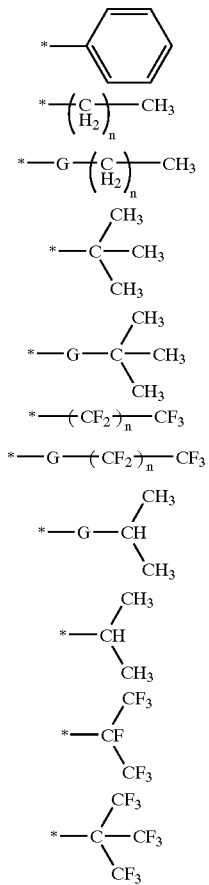

-continued

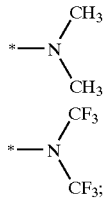

T is a substituent selected from the group consisting of:

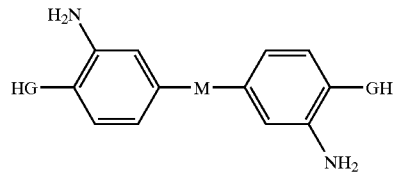

n is an integer from 0 to 5.

2. A bis-o-aminophenol having a formula II

Formula II

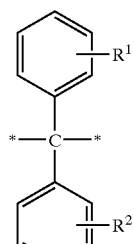

wherein

G is a heteroatom selected from the group consisting of oxygen and sulfur;

M is a substituent selected from the group consisting of:

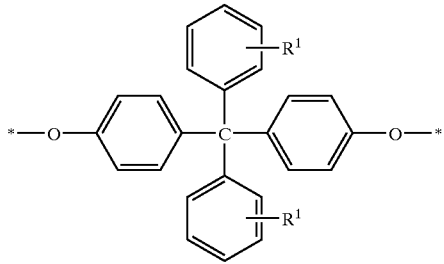

-continued

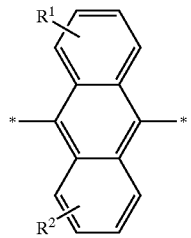

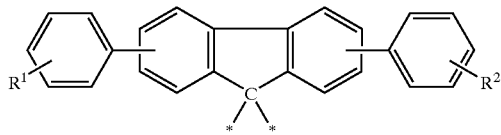

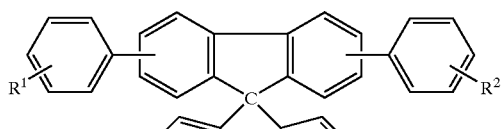

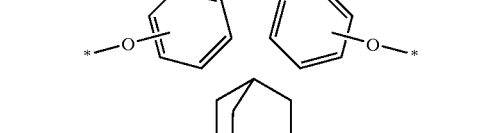

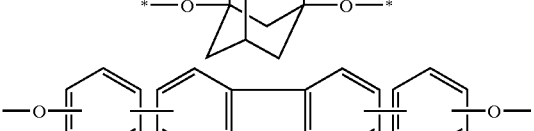

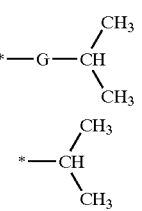

$R^1$, $R^2$, in each case independently, are substituents selected from the group consisting of:

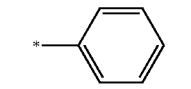

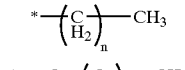

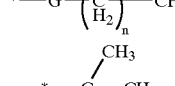

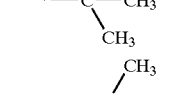

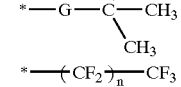

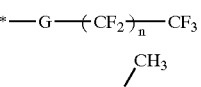

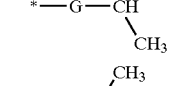

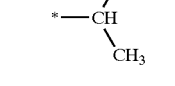

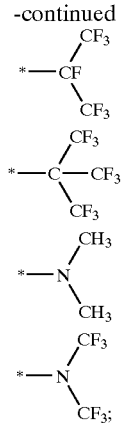

T is a substituent selected from the group consisting of:

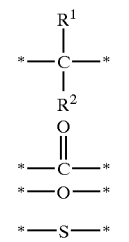

and n is an integer from 0 to 5.

3. The bis-o-aminophenol according to claim 1, wherein G is an oxygen atom.

4. The bis-o-aminophenol according to claim 2, wherein G is an oxygen atom.

5. A process for preparing a bis-o-aminophenol having a formula I

Formula I

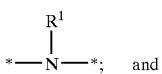

wherein

G is a heteroatom selected from the group consisting of oxygen and sulfur;

M is a substituent selected from the group consisting of:

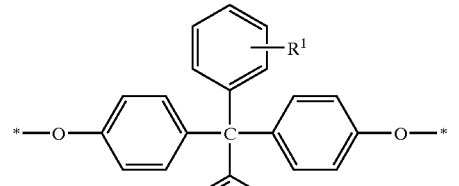
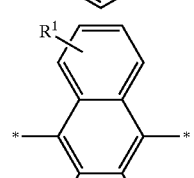
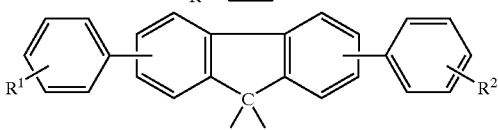
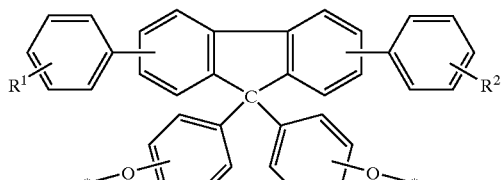
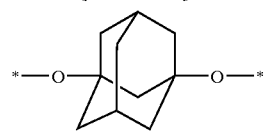
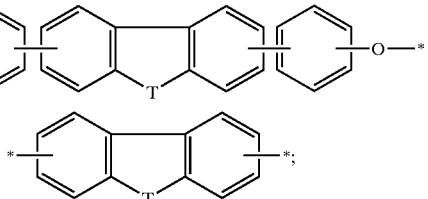

$R^1$, $R^2$, in each case independently, are substituents selected from the group consisting of:

-continued

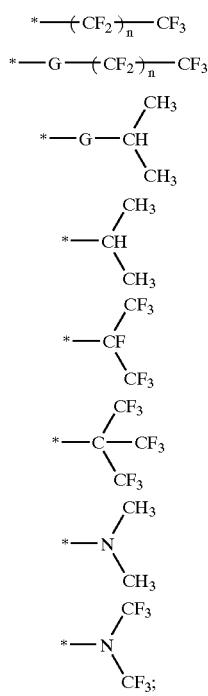

T is a substituent selected from the group consisting of:

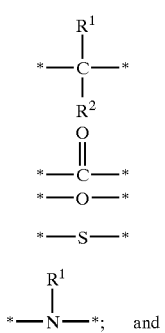

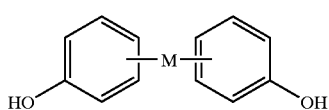

n is an integer from 0 to 5;
the process which comprises:
nitrosating a diol of the formula III Formula III

HO—⟨ ⟩—M—⟨ ⟩—OH with a nitrosating agent to yield a nitroso compound; and
reducing the nitroso compound to the bis-o-aminophenol of the formula I.

6. The process according to claim 5, wherein the nitroso compound is reduced with hydrogen gas with a catalyst.

7. The process according to claim 6, wherein the catalyst is palladium on active carbon.

8. The process according to claim 5, wherein the nitrosating agent is selected from the group consisting of isoamyl nitrite, alkyl nitrite, and a mixture of sodium nitrite and concentrated sulfuric acid.

9. A process for preparing a bis-o-aminophenol having a formula I

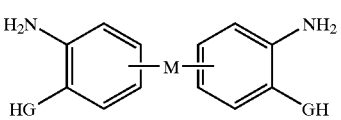

Formula I wherein

G is a heteroatom selected from the group consisting of oxygen and sulfur;

M is a substituent selected from the group consisting of:

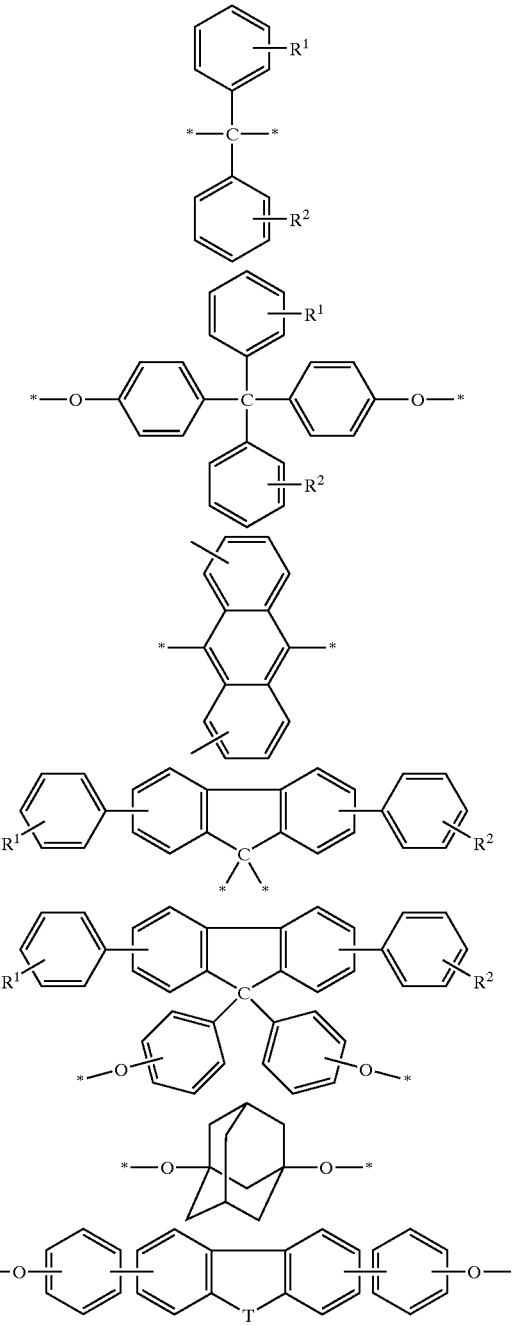

-continued

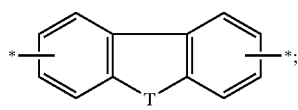

$R^1$, $R^2$ in each case independently, are substituents selected from the group consisting of:

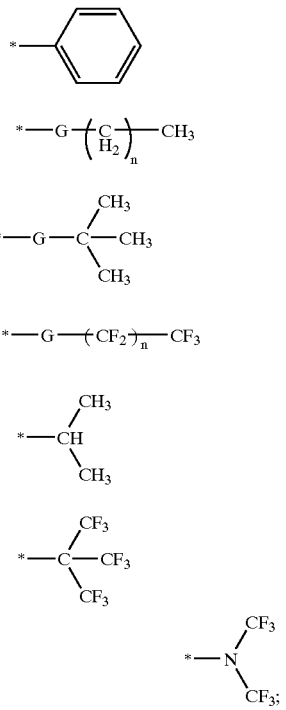

T is a substituent selected from the group consisting of:

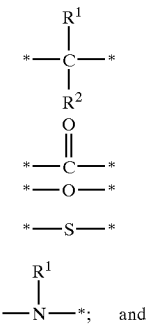

n is an integer from 0 to 5;
the process which comprises:
nitrating a diol having a formula IV

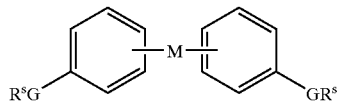

Formula IV a nitrating agent to yield a nitro compound, $R^s$ being a protective group; and
reducing the nitro compound to yield the bis-o-aminophenol of the formula I.

10. The process according to claim 9, wherein the protective group $R^s$ is capable of undergoing reductive elimination.

11. The process according to claim 9, wherein the protective group $R^s$ is a benzyl group.

* * * * *